United States Patent [19]

Dixon

[11] Patent Number: 4,847,851
[45] Date of Patent: Jul. 11, 1989

[54] BUTT-COUPLED SINGLE TRANSVERSE MODE DIODE PUMPED LASER

[75] Inventor: George J. Dixon, Lutz, Fla.

[73] Assignee: University of South Florida, Tampa, Fla.

[21] Appl. No.: 195,850

[22] Filed: May 19, 1988

[51] Int. Cl.[4] ............................................. H01S 3/091
[52] U.S. Cl. ........................................ 372/75; 372/99; 372/49
[58] Field of Search ................ 372/75, 50, 6, 92, 107, 372/108, 98, 21, 99, 49; 350/96.16, 96.15, 96.12

[56] References Cited

U.S. PATENT DOCUMENTS

| | | | |
|---|---|---|---|
| 4,603,421 | 7/1986 | Scifres et al. | 372/50 |
| 4,667,331 | 5/1987 | Alferness et al. | 372/12 |
| 4,728,168 | 3/1988 | Alferness et al. | 372/6 |

FOREIGN PATENT DOCUMENTS

| | | | |
|---|---|---|---|
| 0208189 | 1/1987 | European Pat. Off. | 372/6 |
| 2844129 | 4/1980 | Fed. Rep. of Germany | 372/6 |

*Primary Examiner*—Léon Scott, Jr.
*Attorney, Agent, or Firm*—Harry E. Aine

[57] ABSTRACT

A solid state laser is optically pumped by a semiconductive diode. The output facet of the pumping diode is butt-coupled to the input facet of the laser gain medium. The laser gain medium has a short absorption length (<500 um) for the optical pumping radiation such that the pumped mode volume is so small as to support only a single transverse mode of oscillation, i.e., $TEM_{00}$ mode operation. In one embodiment a reflector of the laser cavity is formed on the output facet of the pumping diode. In another embodiment the input facet of the laser gain material is bonded to the output facet of the diode pump by means of an index-matching optical cement. The resultant diode pumped laser offers improved frequency stability and reduced size.

23 Claims, 1 Drawing Sheet

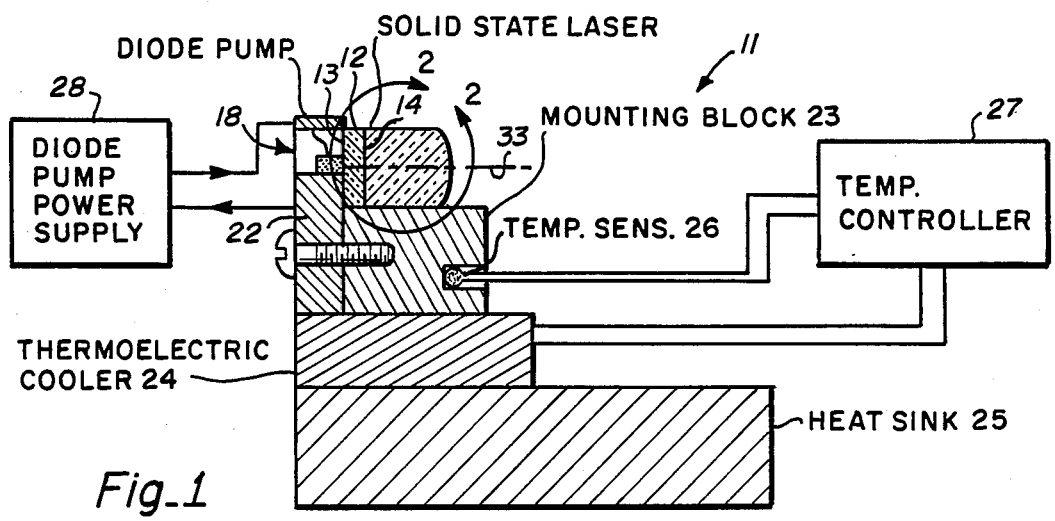
Fig_1
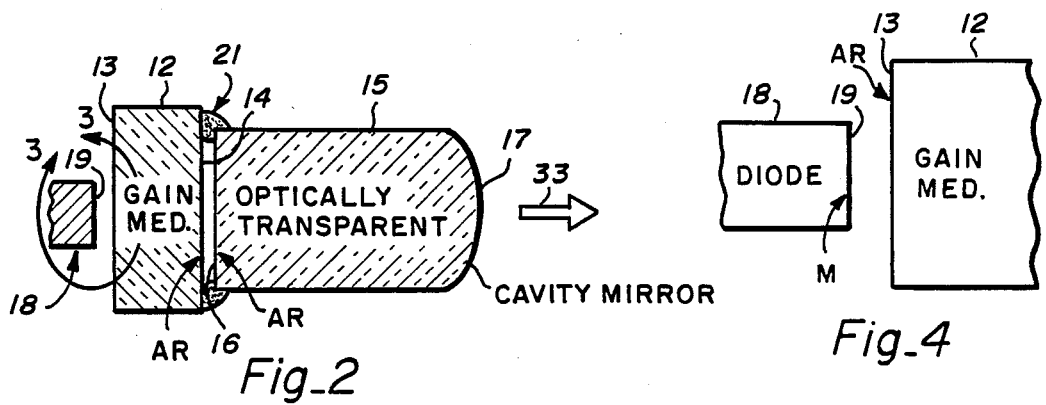
Fig_2 Fig_4
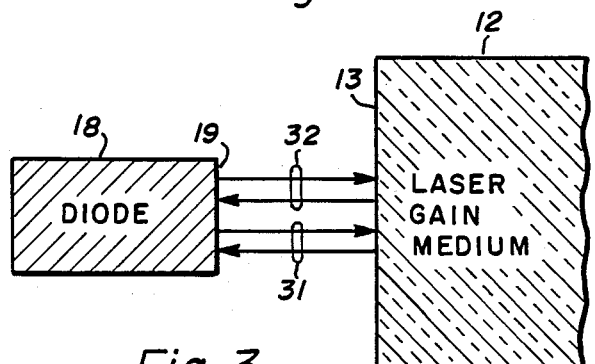
Fig_3
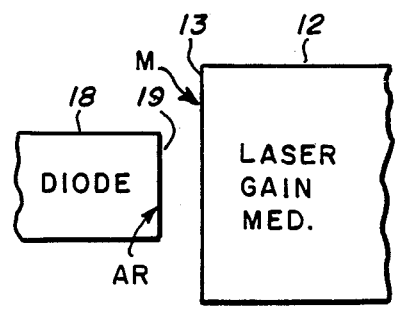
Fig_5
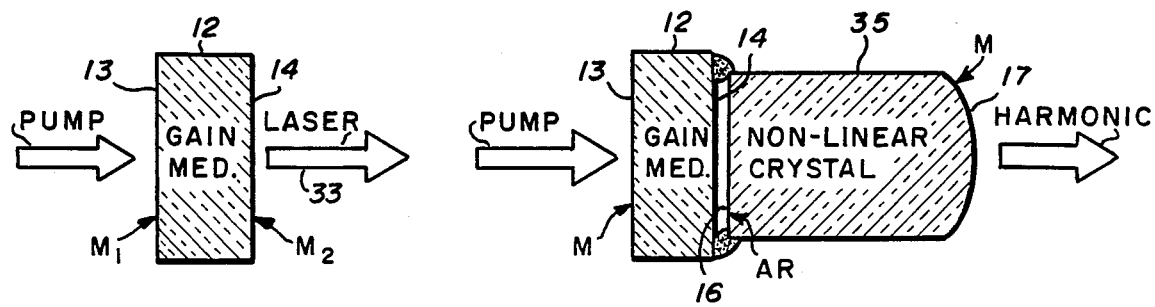
Fig_6 Fig_7

BUTT-COUPLED SINGLE TRANSVERSE MODE DIODE PUMPED LASER

GOVERNMENT CONTRACT

The present invention was made in performance of a contract with the Office of Naval Research and the Government has certain rights therein.

BACKGROUND OF THE INVENTION

The present invention relates in general to diode pumped solid state lasers and, more particularly, to an improved laser wherein the diode pump is butt-coupled to the laser gain material.

DESCRIPTION OF THE PRIOR ART

Heretofore, it has been proposed to end pump a rod of Nd:YAG laser gain material with the output beam of a laser diode array closely spaced to the end of the rod for efficient coupling of the pumping radiation into the laser gain material. It was also proposed to provide a low f-number light collecting lens or such fiber optics between the diode pump and the end of the rod to facilitate collection of the pumping radiation and direction of the pumping radiation into the rod.

Such a laser is disclosed in U.S. Pat. No. 3,982,201 issued Sept. 21, 1976.

One of the problems with this prior art laser is that the pumping radiation emanating from the output facet of the diode pump has a cone of divergence falling within the range of 30° to 40°. Thus, in the absence of a focusing element between the diode output facet and the input facet to the laser gain material, the pumping light pumps a relatively large mode volume of the laser gain material. In the prior art laser, the sides of the laser rod were polished for internally reflecting the pumping radiation back into the rod so that the pumping radiation would essentially pump the entire volume of the rod, which was approximately 1" in length. In such an arrangement, the pumped mode volume is sufficiently large in transverse cross-sectional area to support higher order transverse modes of oscillation within the laser cavity. As a result, in the absence of mode suppression techniques, the output of the laser will not be a single transverse mode but will include higher order modes. It is desirable to obtain a single transverse mode of operation on the fundamental $TEM_{00}$ mode.

Others have proposed to confine the pumped mode volume to a small cross-sectional area of the laser gain medium by making the laser gain medium of a guided wave fiber of a diameter on the order of 150 microns. In such fiber lasers, it has been proposed to place the output facet of the semiconductive diode pump in close proximity to the end of the fiber such that the pump radiation propagates through the guided wave medium and gain medium and is confined by it. Such a fiber laser is disclosed in an article titled: "Monolithic Nd:YAG Fiber Laser" appearing in Optics Letter Vol. 11, No. 7, pp. 437–439.

Use of imaging elements between the pumping diode and the laser gain medium, as disclosed in the aforecited U.S. Patent, increase the complexity of the diode pumped laser. Two alignment operations are necessary to produce laser action. First, the imaging or focusing element must be properly aligned with respect to the output facet of the laser diode and, secondly, the solid state laser gain medium must be properly aligned with the diode-lens combination. Both of these operations require motion along three orthogonal axes. It is desirable to eliminate the cost and complexity of the alignment mechanisms.

The diode pumped fiber lasers can utilize butt-coupling techniques. However, the fabrication of fiber lasers requires highly complex crystal growth and polishing techniques.

SUMMARY OF THE PRESENT INVENTION

The principal object of the present invention is the provision of an improved single transverse mode diode pumped laser.

In one feature of the present invention, the output facet of the diode pump is butt-coupled (closely coupled) to an input facet of the laser gain medium and the laser gain medium it selected to have a very short absorption length for the optical pumping radiation, i.e., less than 500 micrometers, such that a sufficiently small volume of laser gain material is pumped so as to excite essentially only a single transverse mode of laser oscillation within the laser gain medium and optical resonator containing same.

In another feature of the present invention, the output reflector for a diode laser pump and the input reflector for a solid state laser are coated on a common surface, either the output facet of the diode, or, the input facet of the solid state laser, whereby back reflections are eliminated which can produce amplitude and frequency instabilities of the solid state laser.

In another feature of the present invention, the output facet of the diode pump is butt-coupled to an input facet of the laser gain material by a layer of index-matching optical adhesive, whereby the size and complexity of the resultant laser are substantially reduced.

In another feature of the present invention, the laser gain medium includes parallel planar input and output faces with the output face having a reflective coating deposited thereon to form the output mirror of an optical resonator containing the laser gain medium, whereby the laser gain medium comprises a Fabry-Perot cavity and the resultant laser is of reduced size and complexity.

In another feature of the present invention, an optically transparent member is fixedly secured to the laser gain medium and an output facet of said optically transparent member is coated to provide one of the reflectors of the laser cavity containing the laser gain medium, whereby the size and construction of the laser is reduced in use.

In another feature of the present invention, an optically non-linear member is fixedly secured to the laser gain with an output facet of the non-linear material being coated to define an output mirror of the laser cavity, whereby a harmonic generator is obtained of reduced size and complexity.

In another feature of the present invention, an optically transparent member is fixedly secured to the laser gain medium and coated with a reflective coating to define an output mirror member is made of a material having a temperature coefficient of optical pathlength therethrough of opposite sign to that of the laser gain medium, whereby the overall temperature coefficient for the output frequency of the laser is reduced in use.

Other features and advantages of the present invention will become apparent upon a perusal of the following specification taken in connection with the accompanying drawings wherein:

BRIEF DESCRIPTION OF THE DRAWINGS

FIG. 1 is a longitudinal sectional view, partly in block diagram form, of a diode pumped laser incorporating features of the present invention, FIG. 2 is an enlarged sectional view of a portion of the structure of FIG. 1 delineated by line 2—2, FIG. 3 is an enlarged detail view of a portion of the structure of FIG. 2 delineated by line 3—3, FIG. 4 is a view similar to that of FIG. 3 depicting an alternative embodiment of the present invention, FIG. 5 is a view similar to that of FIG. 4 depicting an alternative embodiment of the present invention, FIG. 6 is a longitudinal sectional view of an alternative gain medium of the present invention, and FIG. 7 is a view similar to that of FIG. 2 depicting an alternative embodiment of the present invention.

DESCRIPTION OF THE PREFERRED EMBODIMENTS

Referring now to FIGS. 1 and 2, there is shown a diode pumped solid state laser 11 incorporating features of the present invention. A slab of laser gain material 12 having input and output broad faces 13 and 14 has mounted thereto, in closely spaced relation, an optically transparent rod 15, as of fused quartz. The fused quartz member 15 has an input face 16 and an output face 17. The output face is curved with a radius of curvature as of 1 centimeter and is coated with an optical coating so as to form the output mirror of an optical resonator defined between mirror surface 17 and the input face 13 of the laser gain medium 12 which has been similarly coated with a coating to be optically reflective at the laser wavelength.

An optical pumping diode 18 has its output facet 19 disposed in butt-coupled relationship to the input facet 13 of the laser gain medium. As used herein, "butt-coupled" is defined to mean a coupling sufficiently close, i.e., less than 0.001", such that the divergent beam of optical pumping radiation emanating from the output facet 19, and essentially on the optical axis of the laser resonator, will optically pump a mode volume within the medium with sufficiently small transverse cross-sectional area so as to support essentially only single transverse mode laser operation, i.e., $TEM_{00}$ mode operation. This is accomplished when the laser gain medium 12 has a relatively short absorption length for the pumping radiation, i.e., 63% of the optical pumping radiation passing through the input facet 13 is absorbed within a pathlength of less than 500 microns within the laser gain medium. The absorption length is chosen and the spacing between the output facet 19 of the pumping diode 18 is chosen such that the pumped mode volume within the gain medium 12 has a transverse cross-sectional area sufficiently small to support laser oscillation on only a single transverse mode, i.e., $TEM_{00}$ mode. The divergent lobe of pumping radiation is aligned to be essentially collinear with the optical axis of the optical resonator defined between mirrors 13 and 17. The optically transparent member 15 is fixedly secured to the output face 14 of the gain medium 12 by means of a suitable adhesive bead at 21.

The diode pump 18 is fixedly secured to a mounting member 22, as of copper, which in turn is screwed, or otherwise fixedly attached, to a mounting block 23, as of copper. The laser gain medium 12 and the optically transparent rod 15 are fixedly secured to the mounting block as by adhesive. Mounting blocks 22 and 23 are maintained at a desired temperature by means of a thermal electric cooler 24. The hot face of thermoelectric cooler 24 is mounted in heat-exchanging relation with a heat sink 25. A temperature sensor 26, such as a thermistor, is mounted within the mounting block 23 for sensing its temperature. A temperature controller 27, responsive to the output of the temperature sensor maintains the cold face of the thermoelectric cooler 24 at the desired temperature. A diode pump power supply 28 supplies current to the diode pump 18.

In a typical example, the diode pump 18 is a laser diode of the single-stripe type either gain or index guided with output power in the range of 5 to 40 mW. The output frequency of the diode pump 18 is matched to a strong absorption line in the solid state gain medium 12 by varying the temperature and/or current supplied to it. The diode current may be constant in value or modulated to produce relaxation of spike-mode oscillations in the solid state laser.

An example of a suitable laser diode 18 is the SDL-1400-C manufactured by Spectra Diode Labs of San Jose, Calif. A suitable temperature controller 27 is disclosed in Electronics Device News, June 20, 1977, pg. 90, FIG. 6, and a suitable thermoelectric cooler 24 is the Frigichip Model FC-0.6-32-06L, commercially available from Melcor Industries.

A typical example of the laser gain medium 12 is one having an absorption length for the diode pumping radiation of less then 75 microns and is polished flat and parallel on faces 13 and 14 to accuracies typical of intracavity laser optics. Thicknesses of the gain material 12 may vary from 0.1 to 2 millimeters. A dielectric reflecting coating is applied to input face 13 which transmits greater than 85% of the diode pumping radiation and reflects more than 99.5% of the laser radiation emanating within the gain medium 12. The output face 14 of the gain medium 12 is coated with a dielectric antireflection coating optimized for the lasant wavelength emanating from the gain medium 12. Transmission of radiation through the output face 14 should exceed 99.5% for the lasant radiation emanating within the member 12. The optically transparent member 15 is also polished to tolerances typical for intra-cavity laser optics. Its input face 16 is flat and is coated with an anti-reflection coating which transmits greater than 99.5% at the lasant wavelength emanating from the gain medium 12. Its output face 17 is polished convex with a radius of curvature from 5 to 40 millimeters and coated with a dielectric coating which reflects 98% to 99.8% of the lasant radiation emanating from the gain medium 12. Gain medium 12 and optically transparent member 15 are fixed together in a rigid housing or alternatively fastened together with a suitable adhesive at 21. Preferably, there is a gap exceeding 10 microns in width between the output face 14 of the gain medium and the input face 16 of the optically transparent member 15.

Typically, the laser gain medium 12 comprises a lithium neodymium tetraphosphate crystal, 1 millimeter thick by 2 millimeters square cross-section. The planar faces 13 and 14 are parallel to better than 10 arc seconds. The surface is polished to a polish figure greater than 1/10th of a wavelength. The input face 13 has a reflectivity greater than 99.9% at 1.32 micron with transmission greater than 90% at 800 nanometers, i.e., the pump wavelength. The output face 14 of the gain medium 12 has an anti-reflective coating for 1.32 microns wavelength and its transmission at that wavelength exceeds 99.8%. The optically transparent member 15 is a rod 3 millimeters in length and 3 millimeters in cross-sectional diameter. Its input face 16 is flat and its output face 17 has 1 centimeter convex radius of curvature. The rod 15 is polished to a finish better than 1/10th of a wavelength. The input face 16 is perpendicular to better than one minute and the curvature of the output face 17 is centered to better than 30 microns. The input face 16 has an anti-reflective coating for radiation of a wavelength of 1.32 microns and is transmissive to in excess of 99.8% at 1.32 microns. The output face 17 has a reflective coating which reflects 99.7% at the laser wavelength of 1.32 microns. In the laser of FIG. 1, efficient, low-threshold operation of the diode pumped laser is obtained by maximum intensity of the diode pump radiation and overlap of the absorbed radiation with the lasing mode volume in the laser gain medium 12. Pumping radiation leaving the output facet 19 of the pump, diverges rapidly (15° to 30° full divergence angle is typical).

For efficient operation without the provision of an imaging element between the output facet 19 of the diode pump 18 and the input facet 13 of the gain medium, the pumping radiation should be absorbed within a small distance from the input facet 13 and within the gain medium 12. In such a case, energy is transferred to the laser gain medium before significant divergence of the pump beam can take place. Two conditions need to be fulfilled for efficient operation: (1) the diode output facet 19 should be placed in close proximity to the input facet 13 of the solid state gain medium 12 (i.e., butt-coupled) and (2) the gain medium 12 must have a very strong absorption resonance at the wavelength of the pumping radiation.

Referring now to FIG. 3, back reflection of the diode pump radiation from the input facet 13 of the laser gain medium 12, is shown at 31 and back reflection of solid state laser radiation emanating from the gain medium and reflecting from the diode output facet 19 is shown at 32. These two sources of back-reflection are significant causes of amplitude and frequency instability in the output of the solid state laser at 33. These amplitude and frequency instabilities are dependent on the intensity and phase of the radiation reflected back into the output facet 19 of the diode pump. Semiconductor laser diode pumps 18 are especially sensitive to this form of perturbation due to a combination of high gain and large output coupling. Diode fluctuations produce relaxation oscillations in the solid state laser 12 which appear as a sinusoidal modulation on the output beam 33. Back reflections from the solid state gain medium at 32 also produce instabilities but the situation is somewhat better in that the input face 13 of gain medium is a high reflector at the laser wavelength.

Referring now to FIG. 4, there is shown an alternative embodiment of the present invention in which undesired back reflections are eliminated. More particularly, in the embodiment of FIG. 4, the output reflector for the diode laser 18 and the input reflector for the gain medium 12 are coated on a common surface, either the diode facet 19 or the input facet 13 of the gain medium 12. In the embodiment of FIG. 4, the diode output facet 19 has a dielectric coating applied to it with reflectivity between 0% and 70% at the diode pumping wavelength and 99% to 99.9% at the lasant wavelength of the laser gain medium. The exact value of the diode reflectivity depends on the optimum value for the particular diode being used. Front facet 13 of the solid state gain medium 12 is anti-reflective coated for both wave lengths, i.e., pump and laser so that the transmission exceeds 99%.

In the embodiment of FIG. 5, the coatings are reversed relative to the embodiment of FIG. 4. More particularly, the common reflectors are coated on the input facet 13 of the gain medium and the anti-reflection coatings are applied to the output facet 19 of the diode 18. Reflectivity values are identical to those of the embodiment of FIG. 4 and the distance between the output facet 19 and the input facet 13, in this case, must be less than 10 micrometers.

The common reflective coatings of FIGS. 4 and 5 eliminate back reflections since the diode radiation is absorbed before it can be reflected by the laser gain medium and for most wavelengths, the same is true for the laser radiation emanating from the laser gain medium.

In both embodiments of FIGS. 4 and 5, the output facet 19 of the pumping diode 18 and the input facet 13 of the laser gain medium 12, may be bonded together by a suitable optical adhesive. In a preferred embodiment, the optical adhesive is index matching for the diode index of refraction and the gain material index of refraction and fills the space between the facets 19 and 13. In the case where the index-matching optical cement is used between the facets 19 and 13, the anti-reflection coatings may be eliminated. In this latter embodiment, utilizing the optical cement, a compact composite structure is obtained which is advantageous from the standpoint of device stability. In addition, the size of the device is reduced.

Referring now to FIG. 6, there is shown an alternative embodiment wherein the laser gain medium 12 has reflectors formed on opposite major faces of the medium at 13 and 14 to define a plane Fabry-Perot optical resonator. Input face 13 of the gain medium is coated to be highly reflective for the laser radiation emanating within the member 15 and highly transmissive for the pump radiation passing through the input facet 13. The output facet 14 is coated for 98% to 99.9% reflectivity at the wavelength of the laser radiation emanating from the gain medium. With appropriate changes in the coatings on the input face 13 and on the output facet of the diode 19, as previously described with regard to FIGS. 4 and 5, the common mirror embodiments of FIGS. 4 and 5 are achieved. In these latter embodiments, with the laser gain medium 12 bonded directly to the output facet 19 of the diode 18 by means of the optical matching cement, lasers are obtained which are not much larger than the pump diodes themselves.

Referring now to FIG. 7, there is shown a harmonic generator incorporating features of the present invention. More particularly, the structure of FIG. 7 is essentially the same as that previously described with regard to FIG. 2 with the exception that the optically transparent member 15 is replaced by an optically non-linear crystal 35. The non-linear crystal is phase matched for frequency doubling of the laser frequency generated within the gain medium 12. KTP or MgO:LiNbO$_3$ are typical materials for the non-linear crystal 35. Input face 13 of the laser gain medium 12 is coated for high reflectivity at the laser wavelength of 1.048 micrometers. Facets 14 and 16 are anti-reflection coated for high transmission at the laser wavelength and the output face 17 is coated for high reflectivity at the laser wavelength and high transmission at the harmonic such as, for example, the second harmonic at 524 nm.

In the laser of FIGS. 1 and 2, the overall temperature coefficient for the laser can be reduced by making the optically transparent member 15 of a material having a temperature coefficient of optical pathlength of opposite sign to that of the coefficient of the gain medium 12. In this manner, the overall optical pathlength within the optical resonator defined by faces 13 and 17, can be made to have a temperature coefficient that is near zero. This reduced temperature coefficient makes the frequency of laser emission much less sensitive to changes in temperature.

As thus far described, the diode pump 18 has been described as a laser diode. This is not a requirement as the diode pump may be merely a superluminescent diode. In the case where a superluminescent diode is utilized as the pump 18, the outputspectral widths of the pumping beam are approximately the same as the line widths for absorption of pumping radiation in the stoichiometric neodymium materials, i.e., 5 to 10 nm. Because the superluminescent diode is not actually a laser, it is insensitive to back reflections. While back reflections of radiation of the wavelength emanating from the output facet 19 of the diode may cause some instabilities, a substantial improvement in frequency and amplitude stability is obtained by using the superluminescent diode as a pump. In the case where the superluminescent diode 18 is the pump, the output facet 19 of the diode 18 is butt-coupled to the input facet 13 of the laser gain medium without special coatings. Additionally, the input mirror to the optical resonator can be coated on the output facet 19 of the superluminescent diode 18. However, such coatings would be highly reflective at the wavelength of the laser gain medium and highly transmitting (>99.7%) at the wavelength of the pumping radiation. Under these circumstances, the diode 18 would operate as a superluminescent diode.

Laser gain materials 12 which meet the requirements of high absorption of the diode pump radiation include the stoichiometric neodymium compounds, highly doped Nd:glasses and high concentration materials in which the lasing ion is Er, Ho, Tm or Yb Such media may contain one or more sensitizing agents which increase absorption or aid in the de-population of the lower laser level. Stoichiometric crystals include neodymium pentaphosphate, neodymium aluminum borate, lithium neodymium tetraphosphate and others in which the neodymium is a part of the chemical compound from which the crystal is made. Such crystals are described in a text titled: "Current Topics in Material Science", Vol. 4, edited by E. Kaldis, North Holland (1980) in the chapter entitled, "Miniature Neodymium Lasers" by G. Huber. Highly doped neodymium laser glasses are described in "Concentrated Neodymium Laser Glasses" by B. I. Denker, et al in Soviet Journal of Quantum Electronic, Vol. 11, No. 3, pp. 289-297, (1981). In materials in which neodymium is the active ion, laser emission can occur on transitions near 0.940, 1.06, 1.32 or 1.8 micrometers. The highly doped Er and Ho materials are described in Chapter 7 of "Laser Crystals" by A. A. Kaminskii, pp. 319-354.

The advantage of the present invention is that it permits lasers and harmonic generators to be miniaturized and simplified, and in many cases, made more stable in operation.

What is claimed is:

1. In a method for obtaining single transverse mode lasing of a diode pumped bulk member of laser gain material, the steps of:

arranging a member of laser gain material having an absorption length for optical pumping radiation less than 500 micrometers inside an optical resonator having an optical axis passing through the laser gain material;

butt-coupling the output facet of a semiconductive diode pumping light source to a face of said member of laser gain material and directing a divergent lobe of optical pumping radiation emanating from the diode into the bulk of the laser gain material for optically pumping a sufficiently small volume of laser gain material generally on the optical axis of the resonator so as to excite essentially only a single transverse mode of laser radiation within the laser gain material and optical resonator containing same.

2. The method of claim 1 including the step of:

depositing an optically reflective coating on the output facet of the pumping diode to define an input optical reflector of said optical resonator, said deposited coated being transmissive to optical pumping radiation emanating from said diode and being highly reflective to laser radiation emanating from within said laser gain medium.

3. The method of claim 2 including the step of depositing an anti-reflective coating on the input face of said laser gain material through which the optical pumping radiation enters said laser gain material, said anti-reflective coating being anti-reflective to both the optical pumping radiation and to the laser radiation.

4. The method of claim 4 wherein the reflective coating deposited on said output facet of said pumping diode is also anti-reflective to the optical pumping radiation passing therethrough.

5. The method of claim 1 including the step of:

depositing an optically reflective coating on the input face of said laser gain material to define an input optical reflector of said optical resonator, said deposited coating being transmissive to optical pumping radiation emanating from said diode and being highly reflective to laser radiation emanating from within said laser gain material.

6. The method of claim 3 including the step of depositing an anti-reflective coating on the output facet of said pumping diode, said anti-reflective coating being anti-reflective to both the optical pumping radiation and to the laser radiation.

7. The method of claim 1 wherein the step of butt coupling the output facet of said pumping diode to a face of said member of laser gain material includes the step of:

adhesively bonding said output facet of said pumping diode to said face of said laser gain material with a layer of adhesive being interposed between the diode facet and the bonded face of said laser gain material.

8. The method of claim 7 wherein the layer of adhesive has an index of refraction for matching the index of refraction of said diode facet to the index of refraction of said laser gain material.

9. The method of claim 1 including the step of:

arranging an input optical reflector and an output optical reflector in spaced apart relation on the optical axis to define the optical resonator therebetween, said input optical reflector being transmissive to the optical pumping radiation and being highly reflective to the laser radiation, and said output optical reflector being highly reflective to the laser radiation.

10. The method of claim 9 including the step of: forming the output reflector as a reflective coating on a facet of said laser gain material.

11. The method of claim 9 including the step of:
fixedly securing a second optically transparent member to said laser gain member, and
forming the output reflector as a reflective coating on a facet of said second member.

12. The method of claim 11 including the step of:
making the second member of an optically non-linear material;
interacting the laser radiation with the optically non-linear material to generate harmonic radiation of said laser radiation; and
extracting said harmonic radiation from said optical resonator.

13. The method of claim 11 including the step of:
making the second member of a material having a temperature coefficient of optical pathlength of opposite sign to that of said laser gain material so that the overall optical pathlength through the optical resonator has a reduced temperature coefficient to reduce temperature dependent changes in the wavelength of the laser radiation.

14. In a diode pumped solid state laser:
optical resonator means having a pair of spaced optical reflectors for resonating laser radiation therein and for defining an optical axis of said resonated laser radiation;
laser means for emitting laser radiation in response to absorption of optical pumping radiation;
optical pumping means including a semiconductive diode having an output facet for emitting a divergent beam of optical pumping radiation through said output facet;
said laser gain means including a faceted solid state member of laser gain material having an absorption length for the optical pumping radiation of less than 500 micrometers; and
butt-coupling means for butt-coupling said output facet of said semiconductive diode to an input facet of said faceted solid state member of laser gain material and for directing said divergent beam of optical pumping radiation into said laser gain material generally on said optical axis for optically pumping a sufficiently small volume of said laser gain material so as to excite essentially only a single transverse mode of laser radiation within said laser gain means and optical resonator means.

15. The laser of claim 14 wherein said butt-coupling means is arranged for coupling said output facet of said optical pumping diode to said facet of said laser gain medium with a spacing therebetween of less than 25 micrometers.

16. The laser of claim 14 wherein the laser gain material is selected from the group consisting of stoichiometric neodymium compounds, highly doped Nd:glasses, and high concentration materials in which the lasing ion is Er, Ho, Tm and Yb.

17. The laser of claim 14 wherein one of said optical reflectors of said optical resonator comprises a reflective coating on the output facet of said optical pumping semiconductive diode.

18. The laser of claim 14 wherein one of said optical reflectors of said optical resonator means comprises a reflective coating on one of the facets of said faceted laser gain material which faces the output facet of said optical pumping semiconductive diode 19. The laser of claim 14 wherein said butt-coupling means includes a layer of optically transmissive adhesive for adhesively bonding said output facet of said optical pumping diode to said input facet of said laser gain medium, said adhesive layer being interposed between said bonded facets and disposed such than the optical pumping radiation passes through the adhesive layer, and said adhesive layer having an index of refraction of a value falling in between the index of refraction of said diode facet and that of said input facet of said laser gain material.

20. The laser of claim 14 wherein one of said optical reflectors of said optical resonator means comprises a reflective coating on an output facet of said faceted laser gain material.

21. The laser of claim 14 including a second solid state optically transparent faceted member disposed within said optical resonator means and on the optical axis of said resonator means, said second-member being fixedly secured to said faceted member of laser gain material; and
wherein one of said optical reflectors of said optical resonator means comprises a reflective coating on an output facet of said second member.

22. The laser of claim 21 wherein said second optically transparent faceted member has a temperature coefficient of optical pathlength of opposite sign to that of said laser gain member, whereby temperature dependent changes in the wavelength of the laser radiation are reduced.

23. The laser of claim 21 wherein said second faceted member is an optically non-linear material for interaction with the laser radiation within said optical resonator means for generating harmonic radiation of said laser radiation; and
output coupler means for extracting said harmonic radiation from said optical resonator means.

* * * * *